United States Patent
Lin et al.

(10) Patent No.: US 6,251,580 B1
(45) Date of Patent: *Jun. 26, 2001

(54) SYNTHETIC MEDIA FOR BLOOD COMPONENTS

(76) Inventors: Lily Lin, 80 Hill Rd., Berkeley, CA (US) 94708; Laurence Corash, 1070 Green St., #1900, San Francisco, CA (US) 94133; Jean Marc Payrat, Baxter R & D Europe rue du Progrés N°7, 1400 Nivelles (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/240,067

(22) Filed: Jan. 29, 1999

Related U.S. Application Data

(63) Continuation of application No. 08/692,444, filed on Aug. 5, 1996, now Pat. No. 5,908,742, which is a continuation of application No. 08/338,039, filed on Nov. 14, 1994, now abandoned, which is a continuation-in-part of application No. 08/072,485, filed on Jun. 2, 1993, now Pat. No. 5,459,030, which is a continuation-in-part of application No. 07/926,477, filed on Aug. 7, 1992, now abandoned, which is a continuation-in-part of application No. 07/844,790, filed on Mar. 2, 1992, now Pat. No. 5,288,605.

(51) Int. Cl.$^7$ ........................................ A01N 1/02
(52) U.S. Cl. ..................................... 435/2; 604/4; 604/20
(58) Field of Search ................................ 435/2; 424/532, 424/606, 681, 680, 679; 604/4, 20; 514/455

(56) References Cited

U.S. PATENT DOCUMENTS

| | | |
|---|---|---|
| Re. 32,874 | 2/1989 | Rock et al. . |
| 2,786,014 | 3/1957 | Tullis . |
| 3,629,071 | 12/1971 | Sekhar . |
| 3,729,947 | 5/1973 | Higuchi . |
| 3,735,005 | 5/1973 | Shio et al. . |
| 3,874,384 | 4/1975 | Deindoertes . |
| 4,124,598 | 11/1978 | Hearst et al. . |
| 4,152,208 | 5/1979 | Guirgis . |
| 4,157,723 | 6/1979 | Granzow . |
| 4,169,204 | 9/1979 | Hearst et al. . |
| 4,196,281 | 4/1980 | Hearst et al. . |
| 4,265,280 | 5/1981 | Ammann . |
| 4,344,936 | 8/1982 | Soslau et al. . |
| 4,390,619 | 6/1983 | Harmening-Pittiglio . |
| 4,412,835 | 11/1983 | Spencer . |
| 4,447,415 | 5/1984 | Rock et al. . |
| 4,639,373 | 1/1987 | Babior . |
| 4,695,460 | 9/1987 | Holme . |
| 4,704,352 | 11/1987 | Miripol . |
| 4,727,027 | 2/1988 | Wiesehahn . |
| 4,748,120 | 5/1988 | Wiesehahn et al. . |
| 4,828,976 | 5/1989 | Murphy . |
| 4,878,891 | 11/1989 | Judy . |
| 4,925,665 | 5/1990 | Murphy . |
| 4,960,408 | 10/1990 | Klainer . |
| 4,985,153 | 1/1991 | Kuroda . |
| 4,992,363 | 2/1991 | Murphy . |
| 5,011,695 | 4/1991 | Dichtelmuller . |
| 5,055,485 | 10/1991 | Geacintov . |
| 5,100,564 | 3/1992 | Pall . |
| 5,112,298 | 5/1992 | Prince . |
| 5,120,649 | 6/1992 | Horowitz . |
| 5,234,608 | 8/1993 | Duff . |
| 5,234,808 | 8/1993 | Murphy . |
| 5,288,605 | * 2/1994 | Lin et al. .............................. 435/902 |
| 5,344,752 | 9/1994 | Murphy . |
| 5,372,929 | 12/1994 | Cimino . |
| 5,376,524 | 12/1994 | Murphy . |
| 5,399,719 | 3/1995 | Wollowitz . |
| 5,418,130 | 5/1995 | Platz . |
| 5,456,845 | 10/1995 | Nishimura . |
| 5,459,030 | * 10/1995 | Lin et al. ................................ 435/2 |
| 5,474,891 | 12/1995 | Murphy . |
| 5,482,828 | 1/1996 | Lin et al. . |
| 5,516,629 | 5/1996 | Park . |
| 5,556,958 | 9/1996 | Carroll et al. . |
| 5,559,250 | 9/1996 | Cook et al. . |
| 5,593,823 | 1/1997 | Wollowitz et al. . |
| 5,618,662 | 4/1997 | Lin et al. . |
| 5,665,762 | 9/1997 | Carroll et al. . |
| 5,709,991 | 1/1998 | Lin et al. . |
| 5,712,085 | 1/1998 | Wollowitz et al. . |
| 5,908,742 | * 6/1999 | Lin et al. ................................. 435/2 |

FOREIGN PATENT DOCUMENTS

WO91/03933    4/1991    (WO) .

OTHER PUBLICATIONS

Adams G.A., and Rock G. "Storage of human platelet concentrates in an artificial medium without dextrose" Transfusion 28:217 (1988).

Adams, G.A. et al. "Survival and recovery of human platelets stored for five days in a non–plsma medium" Blood 67:672 (1986).

Alter et al. "Photochemical Decontamination of Blood Components Containing Hepatitis B and Non–A, Non–B Virus." The Lancet (ii:1446–1450) (1988).

Artur M. et al. "Reversible binding of 5– and 8–methoxypsoralen to human serum proteins (albumin) and to epidermis in vitro" Brit. J. Derm. 101:669–677 (1979).

Belogurov and Zavil'gel'skii "Mechanism of the inactivation of the photosensitizer 8–Methoxypsoralen on bacteria and bacteriophages" Sovgenet 14:219–223 (1978).

Ben–Hur E. et al. "Measurement of DNA crosslinks by S1 nuclease: Induction and repair in psoralen plus 360 nm light treated *Escherichia coli*," Photochem. Photobio. 29:921 (1979).

(List continued on next page.)

Primary Examiner—Ralph Gitomer

(57) ABSTRACT

Synthetic media formulations are disclosed for use with blood preparations intended for in vivo use, including synthetic media formulations to be employed in conjunction with the photodecontamination of platelets.

5 Claims, 11 Drawing Sheets

OTHER PUBLICATIONS

Bertolini, F. et al., "Evaluation of platelet concentrates prepared from buffy coats and stored in a glucose free crystalloid medium" Transfusion 29: 605 (1989).

Bertolini, F. et al., "Platelet quality after 15–day storage of platelet concentrates prepared from buffy coats and stored in a glucose–free crystalloid medium" Transfusion 32:9 (1992).

Bertolini, F. et al., "Platelet concentrates stored in synthetic medium after filtration," Vox Sang 67:82–86 (1992).

Bode A.P. and Miller D.T. "Preservation of in vitro function of platelets stored in the presence of inhibitors of platelet activation and a specific inhibitor of thrombin" J. Lab Clin. Med. 111:118 (1988).

Boomgaard, M.N. et al. "In Vitro Evaluation of platelet concentrates, prepared from pooled buffy coats, stored for 8 days after filtration" Transfusion 34:311–316 (1994).

Bordin, F. et al. "5'Methylangelicin: a new highly photosensitizing angular furocoumarin" Experientia 35:1567 (1979).

Bridges, B.A. "8–methoxypsoralen and radiation damage in bacteria" Int'l. J. Rad. Bio. 20:185 (date not available).

Buchholz, D.H. et al. "Bacterial proliferation in platelet products stored at room temperature" New Eng. J. of Med. 285:429–433 (1971).

Buchholz, D.H. et al. "Detection and quantitation of bacteria in platelet products stored at ambient temperature" Transfusion 13:268–285 (1973).

Cinino et al. "Psoralens as Photoactive Probes of Nucleic Acid Structure and Function: Organic Chemistry, Photochemistry, and Biochemistry," Ann. Rev. Biochem. 54:1151–1193 (1985).

Cordle et al. "The sterility of platelet and granulocyte concentrates collected by discontinuous flow centrifugation" Transfusion 30:105 (1980).

Dodd et al. "Inactivation of viruses in platelet suspensions that retain their in vitro characteristics: comparison of psoralen–ultraviolet A and merocyanine 540 visible light methods," Transfusion 31:483–490 (1991).

Fijnheer R. et al. "In vitro evaluation of buffy coat derived platelet concentrates stored in a synthetic medium" Vox Sang. 659:77 (1990).

Friedman L and Stromberg R. "Viral inactivation and reduction in cellular blood products," Rev. Fr. Transfus. Hemobiol. 36:83–91 (1993).

Fujita and Kakishima "Photobiological activities of 5–alkoxypsoralens with respect to the action on E coli" Photochem Photobio. 43:221 (1986).

Gaspairo et al. "Rapid and Sensitive Analysis of 8–MOP in Plasma" J. Invest. Derm. 90:234 (1988).

Grana et al. "Use of 8–methoxypsoralen and ultraviolet pretreated concentrates to prevent Iloimmunization against class I major histocompatibility antigens" Blood 77:2530 (1991).

Grossman, B.J. et al. "Screening blood donors for gastrointestinal illness: a strategy to eliminate carriers to *Yersinia enterocoliticia*" Transfusion 31:500 (1991).

Gulliksson, H. et al. "A system for the supply of platelets suspended in a storage medium including buffy–coat––derived platelet concentrates in combination with "Split" apheresis platelets" Transfusion Sci. 18:1 33–40 (1997).

Gulliksson, H. et al. "Buffy–coat–derived platelet concentrates prepared from half–strength citrate CPD and CPD whole–blood units" Vox Sanguinis 681 152–153 (1995).

Guppy M. et al. "Alternative fuels for platelet storage" Vox Sang 59(3):146 (1990).

Hass and Webb "8–methoxypsoralen effect on survival and repair of *Escherichica coli* after ultraviolet irradiation: action spectra" Radiation Res. 80:170 (1979).

Heal. J.M. et al. "Fatal *Salmonella septicemia* after platelet transfusion" Transfusion 27:2 (1987).

Hearst et al. "The Reaction of the Psoralens with Deoxyribonucleic Acid," Quart. Rev. Biophys. 17:1–44 (1984).

Heaton et al. "Development of a combined storage medium for 7–day storage of platelet concentrates and 42–day storage of red cell concentrates" Brit. J. Haemotology 75:400 (1990).

Holme S et al. "Improved in vivo and in vitro viability of platelet concentrates stored for 7 days in a platelet additive solution" Brit. J. Haemotology 66:233 (1987).

Holme S et al. "Improved platelet in vivo viability follwoing 14 days of storage using a synthetic medium with inhibitors" Blood 74:42a (1989).

Horowitz, B., et al. "Inactivation of viruses in labile blood derivatives," Transfusion 25:516–522 (1985).

Hyde and Hearst, "Binding of Psoralen Derivatives to DNA and Chromatin: Influence of the Ionic Environment on Dark Binding and Photoreactivity," Biochemistry 17:1251–1252 (1978).

Isaacs et al. "A Photochemical Characterization of Reactions of Psoralen Derivatives with DNA,"Trends in Photobiology (Plenum) pp. 279–294 (1982).

Isaacs et al. "Synthesis and Characterization of New Psoralen Derivatives with Superior Photoreactivity with DNA and RNA," Biochemistry 16:1058–1064 (1977).

Joustra–Dijkhuis A.M. "Effect of filtration on subsequently stored platelet concentrates" Vox Sang 67:22–27 (1994).

Kasha M. "Transmission filters for the ultraviolet" J. Optical Soc. Amer. 38:929 (1948).

Knobler R. "Parenteral administration of 8–methoxypsoralen in photopheresis" J. American Acad. Derm. 28:581 (1993).

Kotelba–Witkowska B. "Storage of platelet concentrates using ion exchange resin charged with dibasic phosphate" Blood 58:537 (1981).

Lin et al. "Use of 8–Methoxypsoralen and Long–Wavelength Ultraviolet Radiation for Decontamination of Platelet Concentrates." Blood 74:517–525 (1989).

Lin et al. "Photochemical inactivation of virus and bacteria in platelet concentrates by use of a nobel psoralen and long–wavelength ultraviolet light" Transfusion 37: 423 (1997).

Lin et al. "Photochemical inactivation of pathogenic bacteria in human platelet concentrates" Blood 83:9 pp 2698–2706 (1994).

Lin et al. "Photochemical inactivation of cell–associated human immunodeficiency virus in platelet concentrates" Blood 82:1 pp 292–297 (1994).

Margolis–Nunno et al. "Virus sterilization in platelet concentrates with psoralen and ultraviolet A light in the presence of quencers" Transfusion 32:6 541–547 (1992).

Margolis–Nunno et al. "Photochemical Virus Sterilization in Platelet Concentrates with Psoralen Derivatives." Thromb. Haemostas. 65:1162 (Abstract) (1991).

Meek E et al. "Bacterial prolifertion in human platelet concentrates stored in plasma or artificial medium" ISBT P.F.I.90 (1988).

Melnick J.L. "Viral Hepatitis: One Disease but Multiple Viruses" Abstracts of Virological Safety Aspects of Plasma Derivatives, Cannes France p. 9 Nov. 3–6 (1992).

Metzelaar M.J. "A comparative study on the use of platelet membrane markers for the detection of platelet activation In Vitro and in clinical disorders" Studies on the Expression of Activation Markers on Human Platelets (Thesis) (1991).

Miletic and Popovic "Complement activation in stored platelet concentrates" Transfusion 33:150–154 (1993).

Morel P. et al. "Photochemical Inactivation of viruses and bacteriophage in plasma and plasma fractions" Blood Cells 18: 27–42 (1992).

Moroff et al. "Factors influencing virus inactivation and retention of platelet properties following treatment with aminomethyltrimethylpsoralen and ultraviolet A light" Blood Cells 18:43–56 (1992).

Moroff G. et al. "The influence of irradiation on stored platelets," Transfusion 26:453–456 (1986).

Moroff G. et al. "Factors influencing changes in pH during storage of platelet concentrates at 20–24 C" Vox Sang 42:33–45 (1982).

Morrow et al. "Septic Reactions to Platelet Transfusions." JAMA 266:555–558 (1991).

Murphy and Gardner "Platelet preservation–effect of storage temperature on maintenance of platelet viability—deleterious effect of refrigerated storage" New Eng. J. Med 280:1094 (1969).

Murphy S. et al "Platelet storage in synthetic media lacking glucose and bicarbonate" Transfusion 31:16 (1991).

Murphy S. et al. "Acetate can replace bicarbonate in a platelet storage medium"Transfusion :351a (1991).

Murphy S. et al "Storage of platelet concentrates in plasma and synthetic medium a new polyvinyl chloride container" Transfusion :404a (1991).

Murphy S. et al. "Platelet storage in a synthetic medium" Transfusion 26:568 (1986).

Murphy S. et al. "In vitro assessment of the quality of stored platelet concentrates" Trans. Med. Rev. VIII(I):29–36 (1994).

Myhre, B.A. "Fatalities from blood transfusion" JAMA 244:1333 (1980).

Pietersz R.N. et al. "Platelet concentrates stored in plasma for 72 hours at 22C prepared from buffy coats of citrate phosphate dextrose blood collected in a quadruple bag saline adenine glucose mannitol system" Vox. Sang. 49:81 (1985).

Pindur G. et al. "Hirudin A potential stabilizing factor for platelet preservation in transfusion" Haemostasis 21(SI): 156 (1991).

Rebulla P. et al. "Platelet concentrates prepared from pooled buffy coats and stored in a glucose free crystalloid medium. The Milan experience" Transfusion S. 11:357 (1990).

Ristuccia and Cunha "Klebsiella" Infect. Control 5:343 (1984).

Rock G. et al. "Storage of platelets in balanced salt solutions: a simple platelet storage medium" Transfusion 31:21 (1991).

Stack G. and Snyder E.L. "Storage of platelet concentrate" Blood Sep and Platelet Fractionation (Wiley–Liss, Inc.) pp 99–125 (1991).

Tessman et al. "Photochemistry of the Furan–Side 8–Methoxypsoralen–Thymide Monoadduct Inside the DNA Helix. conversion to Diadduct and to Pyrone–Side Monoadduct," Biochem. 24:1669–1676 (1985).

Thompson et al., "Determination of the Secondary Structure of *Drosophila melanogaster* 5 S RNA by Hydroxymethyl-trimethylpsoralen Crosslinking", J.Mol. Biol. 147: 417–436 (1981).

Thompson et al., "Dependence of 4'–(Hydroxymethyl)–4, 5',8–trimethylpsoralen Photoaddition on the Conformation of Ribonucleic Acid", Biochemistry 21:1363–1368 (1982).

van Marwijk Kooy et al. "Filtration: A method to prepare white cell–poor platelet concentrates with optimal preservation of platelet viability" Transfusion 30:34–38 (1990).

Wadenvik H. et al. "Leukocyte removal filtrationof platelet concentrates A study of platelet loss using In—labeled platelets and dynamic gamma camera scintigraphy" Eur. H. Haematol. 47:192–96 (1991).

Wagner, et al. "Approaches to the reduction of viral infectivity in cellular blood components and single donor plasma" Trans. Med. Rev. V:1 18–32 (1991).

* cited by examiner

SYNTHETIC MEDIA FOR BLOOD COMPONENTS

The present application is a continuation of patent application Ser. No. 08/692,444, Aug. 5, 1996, now U.S. Pat. No. 5,908,742 which is a continuation of patent application Ser. No, 08/338,039, Nov. 14, 1994, abandoned, which is a continuation-in-part of patent application Ser. No. 08/072,485, filed Jun. 2, 1993, now U.S. Pat. No. 5,459,030 which is a continuation-in-part of patent application Ser. No. 07/926,477 filed Aug. 7, 1992, now abandoned which is a continuation-in-part of U.S. application No. 07/844,790, filed Mar. 2, 1992 U.S. Patent No. 5,288,605 issued Feb. 22, 1994.

FIELD OF THE INVENTION

The invention generally relates to synthetic media for use with blood preparations intended for in vivo use, including synthetic media used in conjunction with the photodecontamination of platelets.

BACKGROUND

Whole blood collected from volunteer donors for transfusion recipients is typically separated into its components: red blood cells, platelets, and plasma. Each of these fractions are individually stored and used to treat a multiplicity of specific conditions and disease states. For example, the red blood cell component is used to treat anemia, the concentrated platelet component is used to control bleeding, and the plasma component is used frequently as a source of Clotting Factor VIII for the treatment of hemophilia.

Ideally, all blood cell preparations should be from freshly drawn blood and then immediately transfused to the recipient. However, the logistics of operating a blood donor center preclude this possibility in the vast majority of cases. Transfusions are needed day and night and it is difficult, if not impossible, to arrange for donor recruiting at unusual hours. Consequently, modern blood donor centers must use stored blood products.

In the United States, blood storage procedures are subject to regulation by the government. The maximum storage periods for the blood components collected in these systems are specifically prescribed. For example, whole blood components collected in an "open" (i.e., non-sterile) system must, under governmental rules, be transfused within twenty-four hours and in most cases within six to eight hours. By contrast, when whole blood components are collected in a "closed" (i.e., sterile) system the red blood cells can be stored up to forty-two days (depending upon the type of anticoagulant and storage medium used) and plasma may be frozen and stored for even longer periods.

While red cells are stored in the cold, Murphy and Gardner, New Eng. J. Med. 280:1094 (1969), demonstrated that platelets stored as platelet-rich plasma (PRP) at 22° C. possessed a better in vivo half-life than those stored at 4° C. Thus, more acceptable platelet concentrates could be transfused after storage at room temperature. Until recently, the rules allowed for platelet concentrate storage at room temperature for up to seven days (depending upon the type of storage container). However, it was recognized that the incidence of bacterial growth and subsequent transfusion reactions in the recipient increased to unacceptable levels with a seven day old platelet concentrate. Platelet concentrates may now be stored for no more than five days.

One might believe that it is a relatively simple matter to keep the blood preparation sterile during the manipulations needed to concentrate the platelets. After all, blood bags used for platelet concentrate preparation are in themselves sterile, as are the connected satellite bags. However, bacteria can be introduced by at least two different means.

First, if the donor is experiencing a mild bacteremia, the blood will be contaminated, regardless of the collection or storage method. Adequate donor histories and physicals will decrease but not eliminate this problem. See B. J. Grossman et al., Transfusion 31:500 (1991).

A second, more pervasive source of contamination is the venepuncture. Even when "sterile" methods of skin preparation are employed, it is extremely difficult to sterilize the crypts around the sweat glands and hair follicles. During venepuncture, this contaminated skin is often cut out in a small "core" by a sharp needle. This core can serve to "seed" the blood bag with bacteria that may grow and become a risk to the recipient.

Indeed, many patients requiring platelet transfusions lack host-defense mechanisms for normal clearing and destruction of bacteria because of either chemotherapy or basic hematologic disease. The growth of even seemingly innocuous organisms in stored platelets can, upon transfusion, result in recipient reaction and death. See e.g., B. A. Myhre, JAMA 244:1333 (1980) and J. M. Heal et al., Transfusion 27:2 (1987).

The reports assessing the extent of contamination in platelets have differed in their methods, sample size, and bacterial detection schemes. D. H. Buchholz et al., Transfusion 13:268 (1973) reported an overall level of platelet contamination of 2.4% when a large (>1000 bags) sample was examined and extensive measures were taken for bacterial culturing. While some units were heavily contaminated after just 24 hours of storage, the incidence as a whole varied according to the age of the concentrate and increased with the widespread practice of pooling individual units; over 30% of pools were contaminated at 3 days. See also D. H. Buccholz et al., New Eng. J. Med. 285:429 (1971). While other clinicians suggest lower numbers, recent studies indicate that septic platelet transfusions are significantly underreported. See e.g., J. F. Morrow et al., JAMA 266:555 (1991).

Pre-culturing platelets is not a solution to the bacterial contamination problem. The culture assay takes 48 hours to detect growth. Holding platelet units for an additional two days to await the results of the assay would create, ironically, a smaller margin of safety. See Table 2 in J. F. Morrow et al., JAMA 266:555 (1991). While heavily contaminated units would be detected at the outset, lightly contaminated units would be allowed to grow for two days. Older and potentially more contaminated units would end up being transfused.

Washing the blood cells (e.g., with saline) or filtering the bacteria are also not practical solutions. These techniques are time consuming and inefficient, as they can reduce the number of viable blood cells available for transfusion. Most importantly, they typically involve an "entry" into the storage system. Once an entry is made in a previously closed system, the system is considered "opened," and transfusion must occur quickly, regardless of the manner in which the blood was collected and processed in the first place.

Finally, antibiotics are not a reasonable solution. Contamination occurs from a wide spectrum of organisms. Antibiotics would be needed to cover this spectrum. Many recipients are allergic to antibiotics. In addition, there is an every increasing array of drug-resistant strains of bacteria that would not be inactivated.

In sum, there is a need for a means of inactivating organisms from blood components prior to storage and transfusion in a way that lends itself to use in a closed system. This approach must be able to handle a variety of organisms without harm to the blood product or the transfusion recipient.

SUMMARY OF THE INVENTION

The invention generally relates to synthetic media for use with blood preparations intended for in vivo use, including synthetic media used in conjunction with the photodecontamination of platelets. By the term "synthetic media" the present invention intends to indicate aqueous solutions (e.g., phosphate buffered, aqueous salt solutions) other than those found as natural fluids (e.g., plasma, serum, etc.). However, it is not intended that such synthetic media be used without the benefit of natural fluids. Indeed, in preferred embodiments, mixtures of synthetic salt solutions and natural fluids are contemplated.

The present invention contemplates that the activating means comprises a photoactivation device capable of emitting a given intensity of a spectrum of electromagnetic radiation comprising wavelengths between 180 nm and 400 nm, and in particular, between 320 nm and 380 nm. It is preferred that the intensity is less than 25 $mW/cm^{12}$ (e.g. between 10 and 20 $mW/cm^2$) and that the mixture is exposed to this intensity for between one and twenty minutes (e.g. ten minutes).

By the phrase "the maximum solubility of psoralen in water" the present invention intends a concentration derived experimentally in an aqueous solution in the absence of organic solvents (e.g., DMSO, ethanol, etc.) at approximately room temperature. Concentrations exceeding this level are detected by the presence of precipitate, which is undesirable for intravenous infusion.

A saturated solution of 8-methoxypsoralen can be made by simply dissolving the compound (over a number of hours at room temperature) in distilled water until precipitate is apparent. If the solution is simply centrifuged, the supernatant can have a concentration of over 50 $\mu$g/ml. On the other hand, if the solution is filtered (e.g., glass wool), the concentration of 8-methoxypsoralen has been found to be under 50 $\mu$g/ml. If, instead of centrifuging or filtering, the saturated solution is dialyzed against distilled water (over a number of days at room temperature), the compound is found to have a maximum solubility of approximately 39 $\mu$g/ml. It has been found that, when placed in a container (not glass) to shield the compound from the light, a 0.9% NaCl solution of 8-methoxypsoralen at a concentration of 30 $\mu$g/ml is stable.

When weighing components, some experimental variability is expected. The present invention employs the term "approximately" to reflect this variability. This variability is typically plus or minus 5% and usually less than 10%.

In one embodiment, the present invention contemplates a synthetic platelet storage media, comprising an aqueous solution of: 45–120 mM sodium chloride; 5–15 mM sodium citrate; 20–40 mM sodium acetate; and 20–30 mM sodium phosphate. In a preferred embodiment, the aqueous solution comprises: approximately 86 mM sodium chloride; approximately 10 mM sodium citrate; approximately 30 mM sodium acetate; and approximately 26 mM sodium phosphate. The solution has a pH of approximately pH 7.2 and an osmolarity of approximately 300mOsm/Kg. By not containing glucose or magnesium, the media is readily autoclaved.

DESCRIPTION OF THE INVENTION

Figure 1:
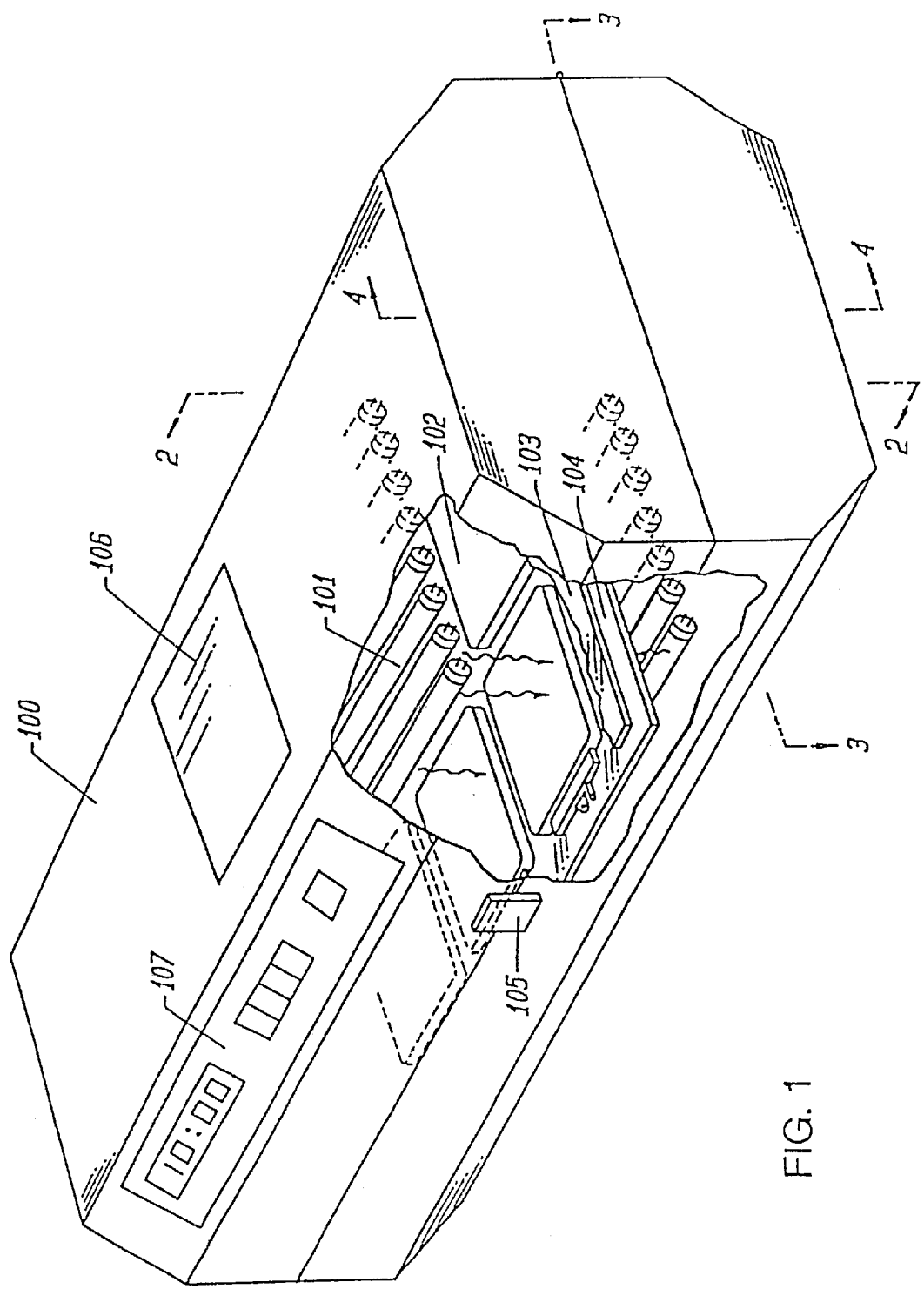
FIG. 1 is a perspective view of one embodiment of the device of the present invention.

The invention generally relates to synthetic media for use with blood preparations intended for in vivo use, including synthetic media used in conjunction with the photodecontamination of platelets.

As noted previously, whole blood is collected and typically separated into red blood cells, platelets, and plasma. Each of these fractions are individually stored under specific conditions prior to in vivo use. In many cases, the extent of contamination is related to the storage time because of growth. A process that inactivated microorganisms at the time of blood collection would be expected to prevent growth during storage.

In one embodiment, the present invention contemplates inactivating blood products after separation but before storage. In this embodiment, a nucleic acid binding compound is selectively employed to treat contamination by microorganisms.

In one embodiment, the nucleic acid binding compound is selected from the group comprising furocoumarins. In a preferred embodiment, the furocoumarin is a psoralen that is activated by a photoactivation device.

Psoralens are tricyclic compounds formed by the linear fusion of a furan ring with a coumarin. Psoralens can intercalate between the base pairs of double-stranded nucleic acids, forming covalent adducts to pyrimidine bases upon absorption of longwave ultraviolet light (UVA). G. D. Cimino et al., Ann. Rev. Biochem. 54:1151 (1985); and Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977); S. T. Isaacs et al., Trends in Photobiology (Plenum) pp. 279–294 (1982); J. Tessman et al., Biochem. 24:1669 (1985); and Hearst et al., U.S. Pat. Nos. 4,124,589, 4,169,204, and 4,196,281, hereby incorporated by reference.

Psoralens have been shown to inactivate viruses in some blood products. See H. J. Alter et al., The Lancet (ii:1446) (1988); L. Lin et al., Blood 74:517 (1989); and G. P. Wiesehahn et al., U.S. Pat. Nos. 4,727,027 and 4,748,120, hereby incorporated by reference, describe the use of a combination of 8-methoxypsoralen (8-MOP) and irradiation. They show that 300 $\mu$g/ml of 8-MOP together with one hour or more of irradiation with ultraviolet light can effectively inactivate viruses. However, these treatment conditions cause harm to the blood product because of energy transfer. Their approach is only feasible if the damage to cells is specifically suppressed by limiting the concentration of molecular oxygen, a difficult and expensive process.

The inactivation method of the present invention provides a method of inactivating single cell and multicellular organisms, and in particular, bacteria, fungi, mycoplasma and protozoa. In addition, the present invention contemplates inactivation of viruses (e.g. HIV virus). In contrast to previous approaches, the method of the present invention does not cause harm to the blood product. There is no significant damage to cells and, therefore, no need to limit the concentration of molecular oxygen.

The present invention contemplates using much lower concentrations of nucleic acid binding compounds than previously employed. For example, the present invention contemplates using 8-MOP at concentrations of 30 $\mu$g/ml or less. Indeed, a preferred concentration of 8-MOP for bacterial decontamination in platelet concentrates is 3 $\mu$g/ml or less, i.e., a one hundred-fold lower concentration than employed by G. P. Wiesehahn et al., supra. Because lower concentrations are employed, solvents like DMSO (used to increase the solubility of 8-MOP) are unnecessary.

The present invention, furthermore, contemplates using much lower doses of irradiation than previously described. This is accomplished with lower intensity irradiation sources, with wavelength cutoff filters (see below), and/or shorter irradiation times. In a preferred embodiment, the time of irradiation is variable and controlled from 1 second to 99 minutes, in one second increments.

In one embodiment, the device of the present invention is mounted on an agitator, giving horizontal unidirectional and sinusoidal motion of variable frequency and amplitude. In another embodiment, heat from the lamps, ballasts and other sources is blocked from the bags.

While it is not intended that the present invention be limited by the theory of inactivation, the use of lower compound concentrations and irradiation doses comes from an understanding that, where the present invention is applied to the decontamination of a single cell or multicellular organism, a lower level of nucleic acid binding will achieve inactivation. In addition, it is recognized that it is not essential that inactivation be complete. That is to say, partial inactivation will be adequate as long as the viable portion is unable, within the storage period, to grow to levels sufficient to cause disease.

To appreciate that, in any given case, an inactivation method may or may not achieve complete inactivation, it is useful to consider a specific example. A bacterial culture is said to be sterilized if an aliquot of the culture, when transferred to a fresh culture plate and permitted to grow, is undetectable after a certain time period. The time period and the growth conditions (e.g., temperature) define an "amplification factor". This amplification factor along with the limitations of the detection method (e.g., visual inspection of the culture plate for the appearance of a bacterial colony) define the sensitivity of the inactivation method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the method appears to be completely effective (and above which the method is, in fact, only partially effective).

This interplay between the amplification factor of an assay and the threshold that the detection method defines, can be illustrated. For example, bacterial cells can be applied to a plate; the detection method is arbitrarily chosen to be visual inspection. Assume the growth conditions and time are such that an overall amplification of $10^4$ has occurred. The detectable signal will be proportional to the number of bacterial cells actually present after amplification. For calculation purposes, the detection threshold is taken to be $10^6$ cells; if fewer than $10^6$ cells are present after amplification, no cell colonies are visually detectable and the inactivation method will appear effective. Given the amplification factor of $10^4$ and a detection threshold of $10^6$, the sensitivity limit would be 100 bacterial cells; if less than 100 viable bacterial cells were present in the original aliquot of the bacterial culture after the sterilization method is performed, the culture would still appear to be sterilized.

Such a situation is common for bacterial growth assays. The sensitivity of the assay is such that viable bacterial cells are present but the assay is unable to detect them. This may explain, at least in part, the variability in results obtained by researchers attempting to determine the extent of bacterial contamination of blood products. See D. H. Buchholz, et al., Transfusion 13:268 (1973), wherein such variability is discussed.

It should be noted that, in many countries, contamination of blood products by cellular organisms is more pervasive and, therefore, more serious than viral contamination. For example, in South America, the most important blood-borne organism is T. cruzi, which is the etiologic agent of Chagas disease. Approximately 16–18 million people are infected in the Americas (including 11% of the population of Chile). It is contemplated that the decontamination method of the present invention is well-suited for inactivation of this protozoa.

The present invention contemplates specific synthetic media formulations for use with blood preparations. The formulations of the present invention are particularly useful for platelet storage. These formulations are also useful when employed in conjunction with the photodecontamination of platelets.

While synthetic media have not previously been employed in conjunction with photodecontamination, synthetic media formulations have been described for platelet storage. For example, U.S. Pat. No. 4,828,976 to Murphy stresses the importance of having a synthetic blood platelet storage medium that is essentially free of glucose and calcium. The specification notes that glucose consumption and lactate production continue as long as glucose is present at the concentration above 1.5 mM (Col. 12, line 13). Lactate production is thought to be the cause of loss of pH stability and consequent impairment of platelet function. See also U.S. Pat. No. 4,925,665 and U.S. Pat. No. 4,992,363.

U.S. Pat. No. 4,447,415 to Rock describes a synthetic medium consisting essentially of: a balanced, physiologically compatible, saline solution; an anticoagulant; and one or more additives to enhance stability of the platelets selected from: (a) nutrients to improve the storage life of the platelets; (b) reversible inhibitors for platelet activation; (c) substances to raise cyclic adenosine monophosphate levels which have reversible effects on platelets; and (d) buffering agents which are physiologically compatible. The specification stresses the need to remove plasma. The specification indicates that this is achieved either by centrifugation and washing, or by "extraction" (see Examples 1 and 2 of the '415 patent). See also U.S. Pat. No. (Reissue) 32,874.

U.S. Pat. No. 4,704,352 to Miripol discloses a medium which contains either magnesium L-ascorbate-2-phosphate or calcium L-ascorbate-2-phosphate. U.S. Pat. No. 4,695,460 to Holme describe media that contain sodium bicarbonate. U.S. Pat. No. 4,390,619 to Harmening-Pittiglio discloses a media capable of supporting platelet metabolism, containing a water-insoluble polymer containing releasable phosphate or bicarbonate ions.

In contrast to these previous attempts, the formulations of the present invention: i) utilize residual plasma; and ii) avoid bicarbonate. With respect to plasma, the present invention contemplates that a standard plasma expression method (e.g., such as currently used in most blood banks) will be used, such that platelets are suspended in a residual plasma concentration between 8 and 25% by volume, and more commonly 12 to 20%. Bicarbonate has been found to be extremely difficult to control in a system employing gas permeable blood bags. The present invention therefore contemplates a phosphate buffer to control the pH of the blood preparation.

The present invention contemplates devices and methods for photoactivation and specifically, for activation of photoreactive nucleic acid binding compounds. The present invention contemplates devices having an inexpensive source of electromagnetic radiation that is integrated into a unit. In general, the present invention contemplates a photoactivation device for treating photoreactive compounds, comprising: a) means for providing appropriate wavelengths of electromagnetic radiation to cause activation of at least one photoreactive compound; b) means for supporting a plurality of blood products in a fixed relationship with the radiation providing means during activation; and c) means for maintaining the temperature of the blood products within a desired temperature range during activation. The present invention also contemplates methods, comprising: a) supporting a plurality of blood product containers, containing one or more photoreactive compounds, in a fixed relationship with a fluorescent source of electromagnetic radiation; b) irradiating the plurality of blood products simultaneously with said electromagnetic radiation to cause activation of at least one photoreactive compound; and c) maintaining the temperature of the blood products within a desired temperature range during activation.

The major features of one embodiment of the device of the present invention involve: A) an inexpensive source of ultraviolet radiation in a fixed relationship with the means for supporting the sample vessels; B) rapid photoactivation; C) large sample processing; D) temperature control of the irradiated samples; and E) inherent safety.

A. Electromagnetic Radiation Source

A preferred photoactivation device of the present invention has an inexpensive source of ultraviolet radiation in a fixed relationship with the means for supporting the sample vessels. Ultraviolet radiation is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g., visible light).

Particular types of ultraviolet radiation are herein described in terms of wavelength. Wavelength is herein described in terms of nanometers ("nm"; $10^{-9}$ meters). For purposes herein, ultraviolet radiation extends from approximately 180 nm to 400 nm. When a radiation source, by virtue of filters or other means, does not allow radiation below a particular wavelength (e.g., 320 nm), it is said to have a low end "cutoff" at that wavelength (e.g., "a wavelength cutoff at 300 nanometers"). Similarly, when a radiation source allows only radiation below a particular wavelength (e.g., 360 nm), it is said to have a high end "cutoff" at that wavelength (e.g., "a wavelength cutoff at 360 nanometers").

For any photochemical reaction it is desired to eliminate or least minimize any deleterious side reactions. Some of these side reactions can be caused by the excitation of endogenous chromophores that may be present during the photochemical activation procedure. In a system where only nucleic acid and psoralen are present, the endogenous chromophores are the nucleic acid bases themselves. Restricting the activation process to wavelengths greater than 320 nm minimizes direct nucleic acid damage since there is very little absorption by nucleic acids above 313 nm.

In blood products, the nucleic acid is typically present together with additional biological chromophores. If the biological fluid is just protein, the 320 nm cutoff will be adequate for minimizing side reactions (aromatic amino acids do not absorb above 320 nm). If the biological fluid includes cells and/or cellular constituents, there will be many other chromophores, including hemes and flavins.

Hemes are abundant in blood products where they arise from the lysis of red cells. Flavins, like hemes, are required for metabolic respiration. Both of these endogenous chromophores will cause damage to cells if excited by photoirradiation.

Hemes have three principle absorption bands: two are in the red region of the visible spectrum; the other is centered about 400 nm. Flavins have two principle absorption peaks: one at 450 nm and the other at 370 nm.

In view of the presence of these endogenous chromophores in blood products, it is intended that the device of the present invention be designed to allow for irradiation within a small range of specific and desirable wavelengths, and thus avoid damage to cells caused by energy transfer. The preferred range of desirable wavelengths is between 320 and 350 nm.

Some selectivity can be achieved by choice of commercial irradiation sources. For example, while typical fluorescent tubes emit wavelengths ranging from 300 nm to above 400 nm (with a broad peak centered around 360 nm), BLB type fluorescent lamps are designed to remove wavelengths above 400 nm. This, however, only provides an upper end cutoff.

In a preferred embodiment, the device of the present invention comprises an additional filtering means. In one embodiment, the filtering means comprises a glass cut-off filter, such as a piece of Cobalt glass. In another embodiment, the filtering means comprises a liquid filter solution that transmit only a specific region of the electromagnetic spectrum, such as an aqueous solution of $Co(No_3)_2$. This salt solution yields a transmission window of 320–400 nm. In a preferred embodiment, the aqueous solution of $Co(No_3)_2$ is used in combination with $NiSO_4$ to remove the 365 nm component of the emission spectrum of the fluorescent or arc source employed. The Co-Ni solution preserves its initial transmission remarkably well even after tens of hours of exposure to the direct light of high energy sources.

It is not intended that the present invention be limited by the particular filter employed. Several inorganic salts and glasses satisfy the necessary requirements. For example, cupric sulfate is a most useful general filter for removing the infra-red, when only the ultraviolet is to be isolated. Its stability in intense sources is quite good. Other salts are known to one skilled in the art. Aperture or reflector lamps may also be used to achieve specific wavelengths and intensities.

When ultraviolet radiation is herein described in terms of irradiance, it is expressed in terms of intensity flux (milliwatts per square centimeter or "mW cm$^{-2}$"). "Output" is herein defined to encompass both the emission of radiation (yes or no; on or off) as well as the level of irradiance. In a preferred embodiment, intensity is monitored at 4 locations: 2 for each-side of the plane of irradiation.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photoactivation, in one embodiment the present invention employs fluorescent sources to achieve results thus far achievable on only expensive equipment.

As used here, fixed relationship is defined as comprising a fixed distance and geometry between the sample and the light source during the sample irradiation. Distance relates to the distance between the source and the sample as it is supported. It is known that light intensity from a point source is inversely related to the square of the distance from the point source. Thus, small changes in the distance from the source can have a drastic impact on intensity. Since changes in intensity can impact photoactivation results, changes in distance are avoided in the devices of the present invention. This provides reproducibility and repeatability.

Geometry relates to the positioning of the light source. For example, it can be imagined that light sources could be placed around the sample holder in many ways (on the sides, on the bottom, in a circle, etc.). The geometry used in a preferred embodiment of the present invention allows for uniform light exposure of appropriate intensity for rapid photoactivation. The geometry of a preferred device of the present invention involves multiple sources of linear lamps as opposed to single point sources. In addition, there are several reflective surfaces and several absorptive surfaces. Because of this complicated geometry, changes in the location or number of the lamps relative to the position of the samples to be irradiated are to be avoided in that such changes will result in intensity changes.

B. Rapid Photoactivation

The light source of the preferred embodiment of the present invention allows for rapid photoactivation. The intensity characteristics of the irradiation device have been selected to be convenient with the anticipation that many sets of multiple samples may need to be processed. With this anticipation, a fifteen minute exposure time or less is a practical goal.

In designing the devices of the present invention, relative position of the elements of the preferred device have been optimized to allow for fifteen minutes of irradiation time, so that, when measured for the wavelengths between 320 and 350 nanometers, an intensity flux greater than approximately 1 mW cm$^{-2}$ is provided to the sample vessels. In a preferred embodiment, the device irradiates both sides of the bag.

C. Processing of Large Numbers of Samples

As noted, another important feature of the photoactivation devices of the present invention is that they provide for the processing of large numbers of samples. In this regard, one element of the devices of the present invention is a means for supporting a plurality of blood products, and in particular, blood bags. In the preferred embodiment of the present invention the supporting means comprises glass plates between two banks of lights with a capacity of six 50 ml bags (equivalent to Dupont Stericell bag) plus connectors and tubing, at one time. By accepting commonly used commercially available blood bags, the device of the present invention allows for convenient processing of large numbers of samples.

D. Temperature Control

As noted, one of the important features of the photoactivation devices of the present invention is temperature control. Temperature control is important because the temperature of the sample in the sample at the time of exposure to light can dramatically impact the results. For example, conditions that promote secondary structure in nucleic acids also enhance the affinity constants of many psoralen derivatives for nucleic acids. Hyde and Hearst, Biochemistry, 17, 1251 (1978). These conditions are a mix of both solvent composition and temperature. With single stranded 5S ribosomal RNA, irradiation at low temperatures enhances the covalent addition of HMT to 5S rRNA by two fold at 4° C. compared to 20° C. Thompson et al., J. Mol. Biol. 147:417 (1981). Even further temperature induced enhancements of psoralen binding have been reported with synthetic polynucleotides. Thompson et al., Biochemistry 21:1363 (1982).

With respect to bacteria, it should be noted that repair of crosslinks occurs during irradiation. However, where a lower temperature is employed during irradiation, the bacterial repair process is suppressed. Thus, a 15° C. irradiation has a significant effect on the level of inactivation that is observed.

E. Inherent Safety

Ultraviolet radiation can cause severe burns. Depending on the nature of the exposure, it may also be carcinogenic. The light source of a preferred embodiment of the present invention is shielded from the user. This is in contrast to the commercial hand-held ultraviolet sources as well as the large, high intensity sources. In a preferred embodiment, the irradiation source is contained within a housing made of material that obstructs the transmission of radiant energy (i.e., an opaque housing). No irradiation is allowed to pass to the user. This allows for inherent safety for the user.

EXPERIMENTAL

In the experimental disclosure which follows, the following abbreviations apply: eq (equivalents) M (Molar); μM (micromolar); N (Normal); mol (moles); mmol (millimoles); μmol (micromoles); nmol (nanomoles); gm (grams); mg (milligrams); μg (micrograms); L (liters); ml (milliliters); μl (microliters); cm (centimeters); mm (millimeters); μm (micrometers); nm (nanometers); ° C. (degrees Centigrade); HPLC (High Pressure Liquid Chromatography).

In some of the examples below, phosphate buffered synthetic media is formulated for platelet storage and treatment. One embodiment is made as follows:

| Ingredients | Amounts (grams/liter) |
| --- | --- |
| Na Acetate.3H$_2$O | 4.08 |
| Citrate.2H$_2$O | 2.94 |
| NaH$_2$PO$_4$.H$_2$O | 0.858 |
| Na$_2$HPO$_4$ | 2.81 |
| NaCl | 5.02 |
| pH adjustment | to pH 7.2 (with HCl) |

Distilled water is added to make 1 liter, the solution is mixed, sterile filtered (0.2 micron filter) and refrigerated.

The following examples serve to illustrate certain preferred embodiments and aspects of the present invention and are not to be construed as limiting the scope thereof.

EXAMPLE 1

As noted above, the present invention contemplates devices and methods for the activation of photoreactive nucleic acid binding compounds. In this example, a photoactivation device is described for decontaminating blood products according to the method of the present invention. This device comprises: a) means for providing appropriate wavelengths of electromagnetic radiation to cause activation of at least one photoreactive compound; b) means for supporting a plurality of blood products in a fixed relationship with the radiation providing means during activation; and c) means for maintaining the temperature of the blood products within a desired temperature range during activation.

FIG. 1 is a perspective view of one embodiment of the device integrating the above-named features. The figure shows an opaque housing (100) with a portion of it removed, containing an array of bulbs (101) above and below a plurality of representative blood product containing means (102) placed between plate assemblies (103, 104). The plate assemblies (103, 104) are described more fully, subsequently.

The bulbs (101), which are connectable to a power source (not shown), serve as a source of electromagnetic radiation. While not limited to the particular bulb type, the embodiment is configured to accept an industry standard, dual bipin lamp.

The housing (101) can be opened via a latch (105) so that the blood product can be placed appropriately. As shown in FIG. 1, the housing (100), when closed, completely contains the irradiation from the bulbs (101). During irradiation, the user can confirm that the device is operating by looking through a safety viewport (106) which does not allow transmission of ultraviolet light to the user.

The housing (100) also serves as a mount for several electronic components on a control board (107), including, by way of example, a main power switch, a count down timer, and an hour meter. For convenience, the power switch can be wired to the count down timer which in turn is wired in parallel to an hour meter and to the source of the electromagnetic radiation. The count down timer permits a user to preset the irradiation time to a desired level of exposure. The hour meter maintains a record of the total number of radiation hours that are provided by the source of electromagnetic radiation. This feature permits the bulbs (101) to be monitored and changed before their output diminishes below a minimum level necessary for rapid photoactivation.

Figure 2:
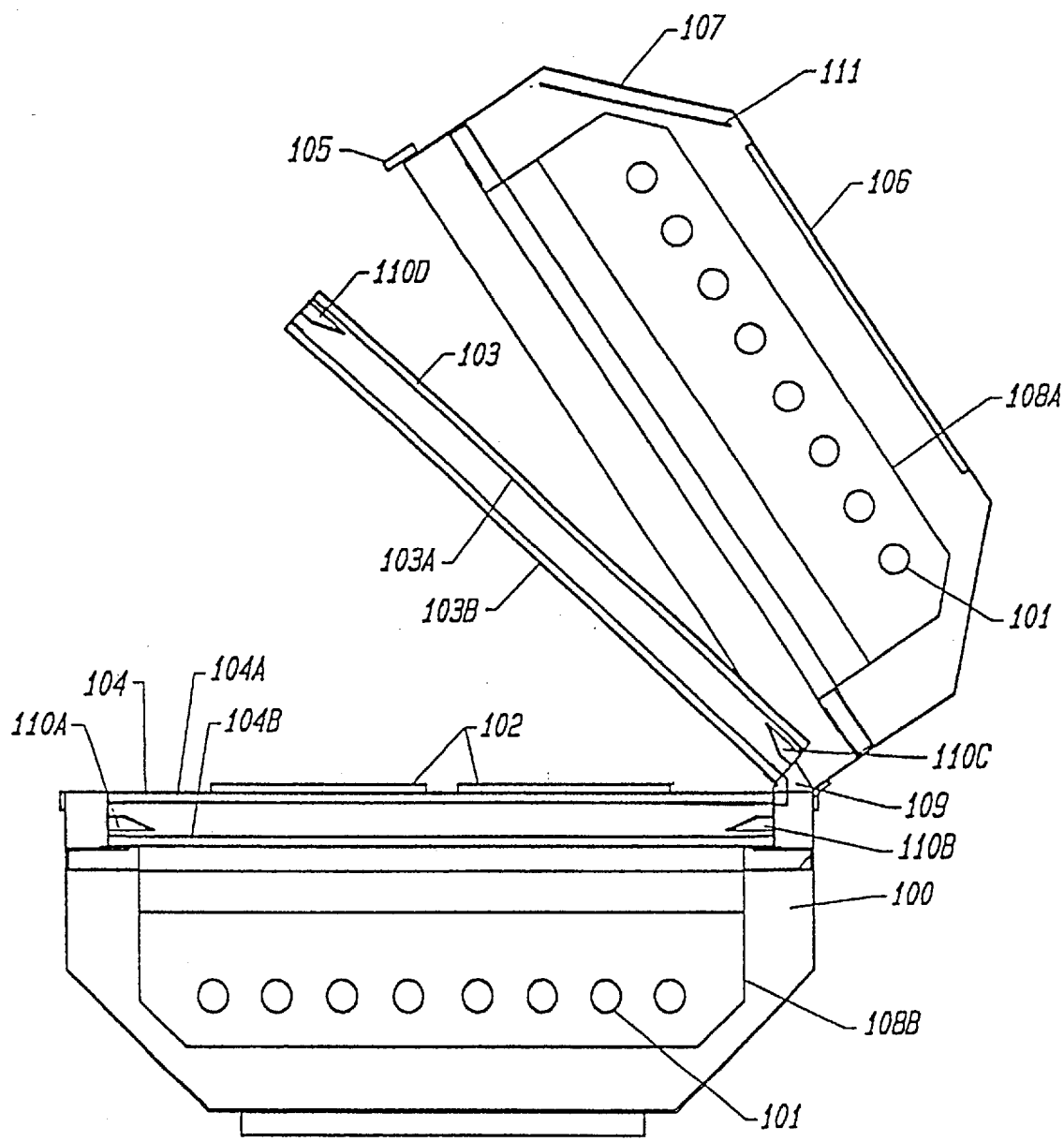
FIG. 2 is a cross-sectional view of the device shown in FIG. 1 along the lines of 2—2.

FIG. 2 is a cross-sectional view of the device shown in FIG. 1 along the lines of 2—2. FIG. 2 shows the arrangement of the bulbs (101) with the housing (100) opened. A reflector (108A, 108B) completely surrounds each array of bulbs (101). Blood product containing means (102) are placed between upper (103) and lower (104) plate assemblies. Each plate assembly is comprised of an upper (103A, 104A) and lower (103B, 104B) plates. The plate assemblies (103, 104) are connected via a hinge (109) which is designed to accommodate the space created by the blood product containing means (102). The upper plate assembly (103) is brought to rest gently on top of the blood product containing means (102) supported by the lower plate (104B) of the lower plate assembly (104).

Detectors (110A, 110B, 110C, 110D) may be conveniently placed between the plates (103A, 103B, 104A, 104B) of the plate assemblies (103, 104). They can be wired to a printed circuit board (111) which in turn is wired to the control board (107).

Figure 3:
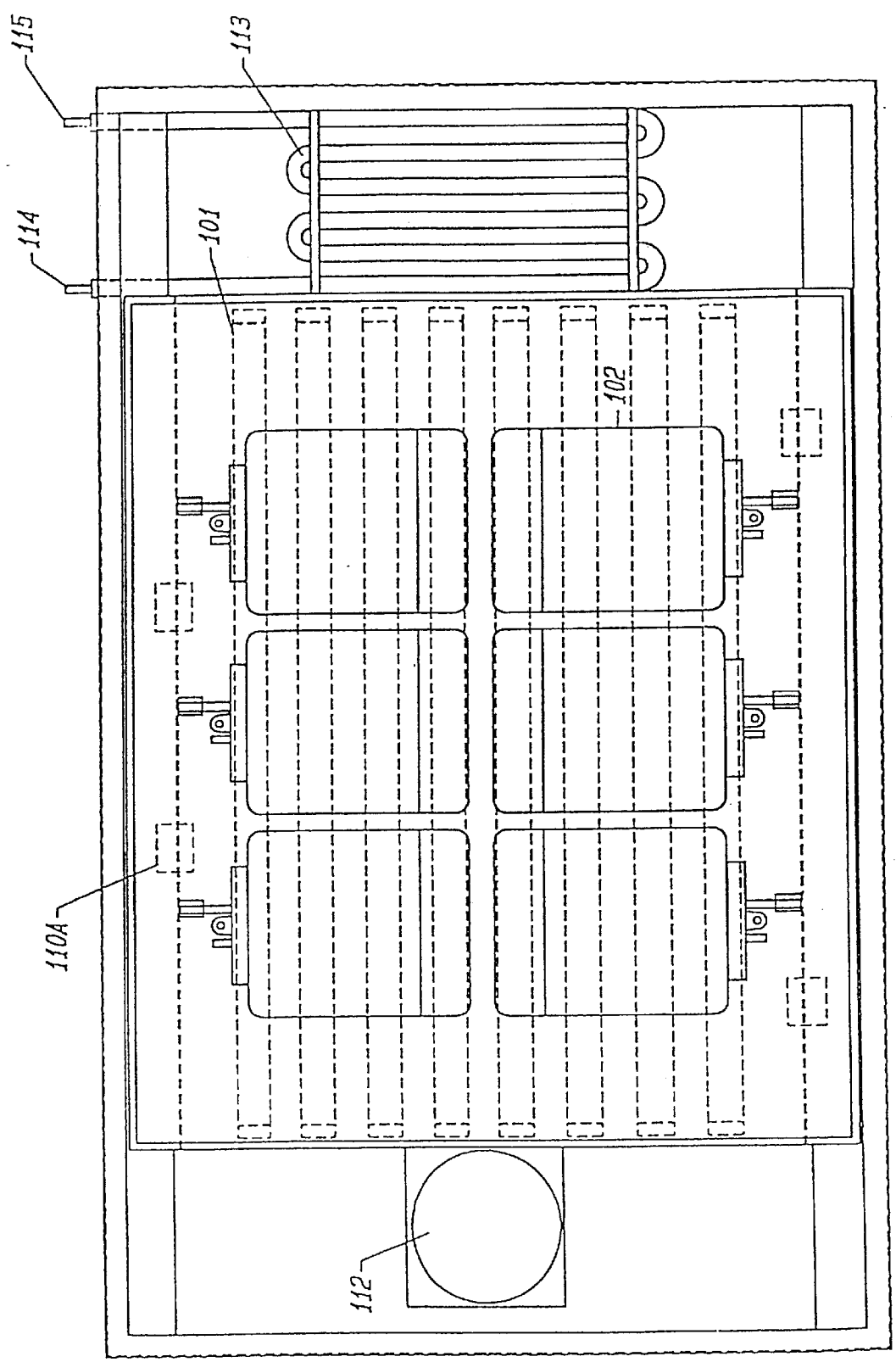
FIG. 3 is a cross-sectional view of the device shown in FIG. 1 along the lines of 3—3.

FIG. 3 is a cross-sectional view of the device shown in FIG. 1 along the lines of 3—3. Six blood product containing means (102) (e.g., Teflon™ platelet unit bags) are placed in a fix relationship above an array of bulbs (101). The temperature of the blood product can be controlled via a fan (112) alone or, more preferably, by employing a heat exchanger (113) having cooling inlet (114) and outlet (115) ports connected to a cooling source (not shown).

Figure 4:
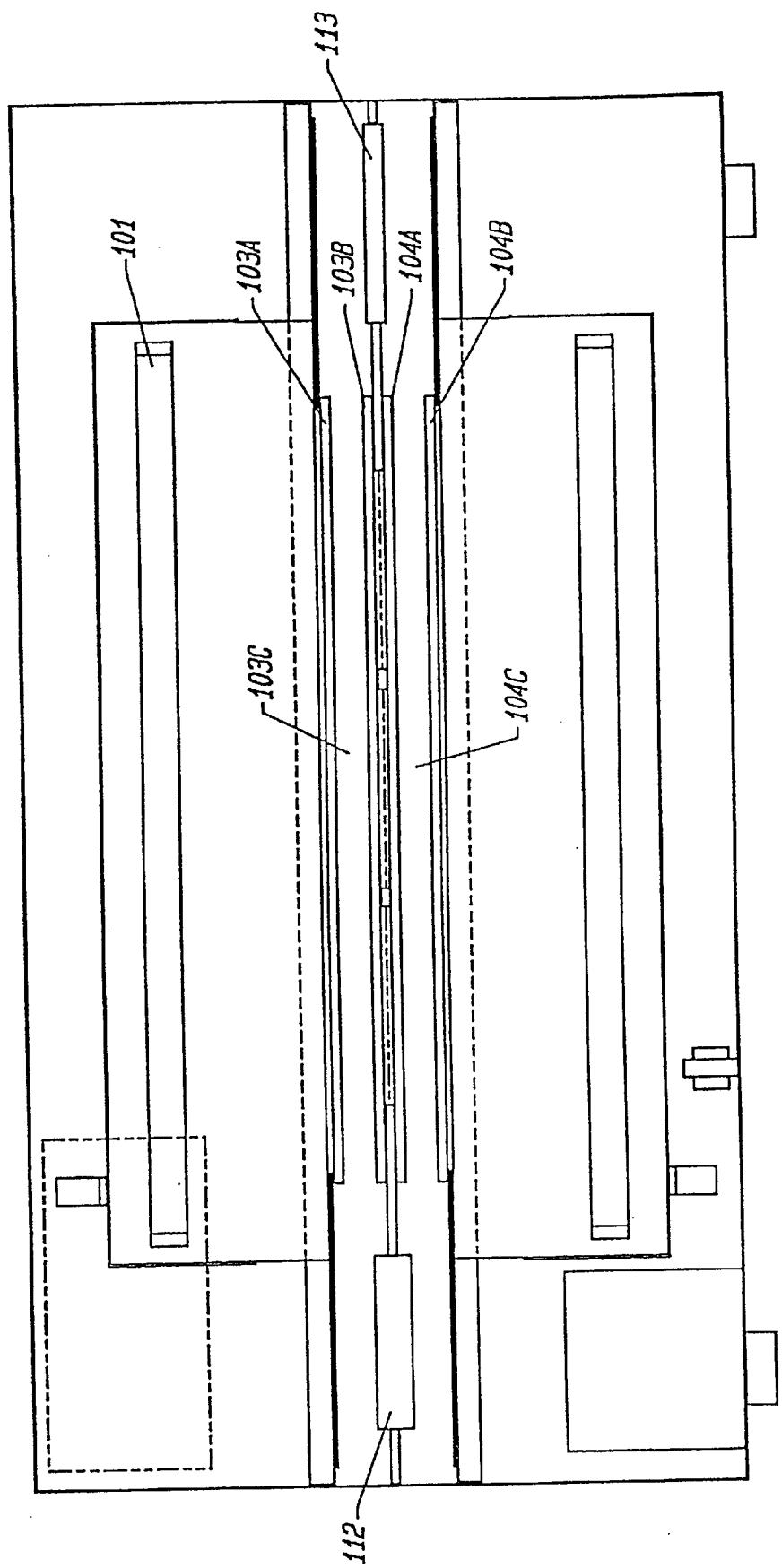
FIG. 4 is a cross-sectional view of the device shown in FIG. 1 along the lines of 4—4.

FIG. 4 is a cross-sectional view of the device shown in FIG. 1 along the lines of 4—4. FIG. 4 more clearly shows the temperature control approach of a preferred embodiment of the device. Upper plate assembly plates (103A, 103B) and lower plate assembly plates (104A, 104B) each create a temperature control chamber (103C, 104C), respectively. The fan (112) can circulate air within and between the chambers (103C, 104C). When the heat exchanger (113) is employed, the circulating air is cooled and passed between the plates (103A, 103B, 104A, 104B).

EXAMPLE 2

Figure 5:
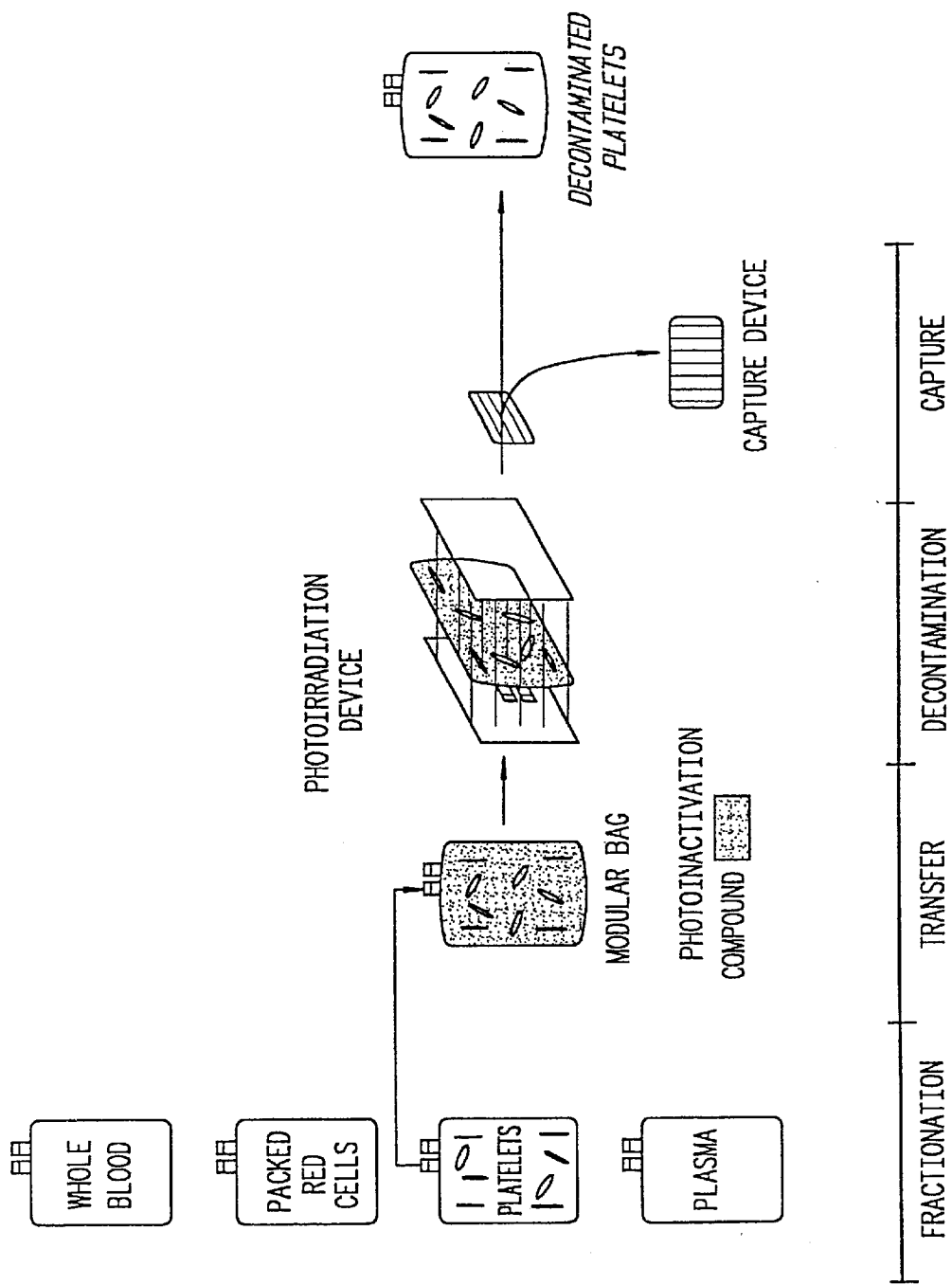
FIG. 5 schematically shows the decontamination approach of the present invention applied specifically to blood products.

FIG. 5 shows an embodiment wherein platelets are treated by the method of the present invention. Following fractionation, platelets are transferred to a bag containing a nucleic acid binding compound (shown in FIG. 5 as a shaded bag). This bag, which has transmission properties and other characteristics suited for the present invention, is then placed in an irradiation device (such as that described in Example 1, above) and is irradiated. The free compound may be collected or "captured" as desired by a capture device. In such a case, the bag would contain only compound that is contained in cells; the bag would have no free compound (this bag is indicated in FIG. 5 as unshaded).

In one capture approach, a bag comprised of a psoralen-binding polymer is employed to capture the compound. The Cutter CLX bag has been found to have this property.

EXAMPLE 3

In this example, the decontamination methods of the present invention are applied to inactivate Klebsiella pneumoniae, which is known to be among the organisms associated with bacteremia. See generally, Infect. Control 5:343 (1984). The particular isolate in this case was obtained following a platelet transfusion where the recipient immediately went into shock and later died. The platelet bag was obtained and cultured, and the organism was identified and serotyped.

For the experiment, the strain was kept at ambient temperature and inoculated onto either heart infusion agar (HIA)

or heart infusion agar containing 5% (v/v) sheep blood (BAP) by swabbing each plate for confluency via a sterile applicator swab. Cultures were then incubated under static conditions for 16–18 h at 35° C. At the end of the incubation period, cultures were removed and suspended in phosphate buffered saline (PBS;pH 7.2–7.4) and spectrophotometrically standardized to 1.0 at an $OD_{610}$ using a Spectronic 501 or 601 spectrophotometer (Bausch and Lomb). After standardization, suspensions were diluted 1:10 in PBS to achieve an ca. $10^8$ CFU/ml concentration. This standardized suspension is then split to use an aliquot for the inactivation study, while another portion was plated in duplicate 10-fold serial dilutions onto HIA (or BAP) to ensure appropriate concentrations of the organism.

To assess inactivation of the organism, two ABO compatible freshly outdated human platelet concentrate units were obtained from the Blood Bank of Alameda—Contra Costa Medical Association. They were pooled and redivided into two bags. One bag was infused with the bacteria preparation. The platelets in the second unit were pelleted at 4000 xg for 6 minutes and then resuspended in a medium containing 85% saline and 15% plasma. Bacteria was added after platelets were well resuspended.

3 ml aliquots of bacteria containing platelet concentrate were transferred to a Teflon™ minibag (American Fluoroseal Corporation, Silver Spring, Md.) and received specified amounts of 8-MOP and UVA irradiation, except for the controls, which were irradiated without psoralen, or received no treatment. Temperature was maintained at 25° C. during irradiation in the irradiation device described above which is equipped with an air cooling mechanism.

F24T 12-BL-HO fluorescent lamps were used. These are high output "black light" tubes (engineered to emit specific wavelengths by means of an internal phosphor coating) 24 inches in length. Total intensity is less than 25 mw/cm² and typically between 15 and 20 mw/cm².

Figure 8:
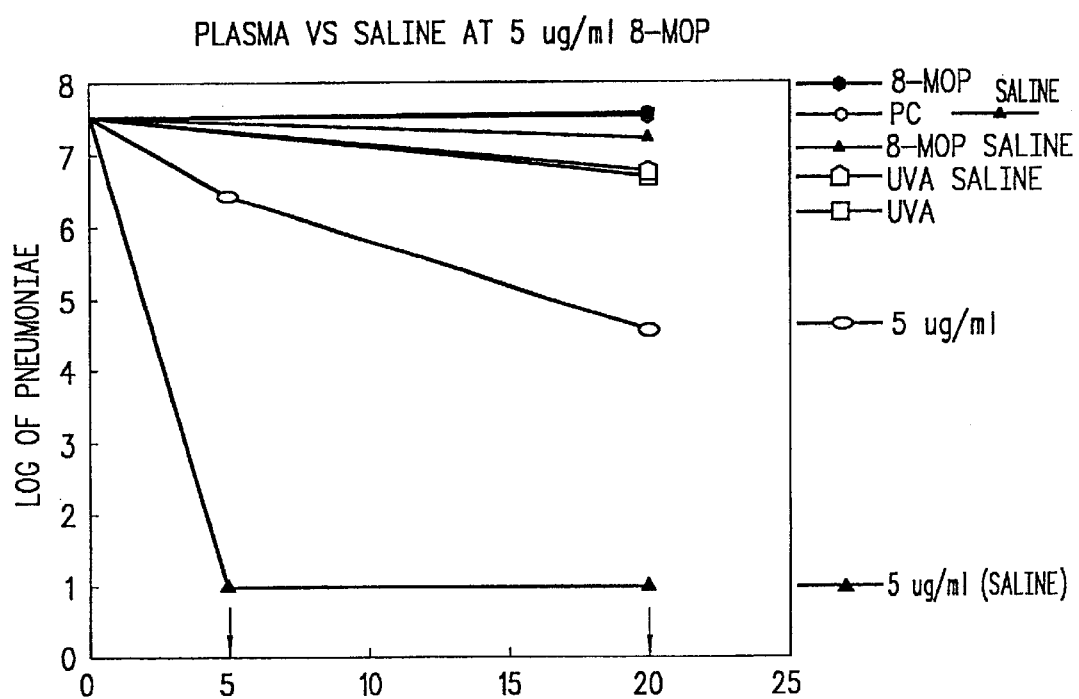
FIG. 8 is a graph showing the inactivation of gram negative bacteria.

Following irradiation, bacteria were quantified by plating 0.1 ml of serial 10-fold dilutions in broth onto 100 mm petri dishes containing BHI agar. After 24 hr incubation at 35° C., colonies were counted and bacterial concentration was calculated on a per ml basis. The results (FIG. 8) show that while only 1.2 logs of Klebsiella were killed by 5 μg/ml 8-MOP in five minutes of UVA irradiation in 100% plasma, more than 6.5 logs were killed under the same conditions in 15% plasma and 85% saline.

While not limited to any theory as to the mechanism by which this improvement in decontamination efficiency was achieved, it would appear that these results indicate that either that the optical properties of the synthetic medium are better, or the lower protein concentration allows for a higher concentration of free 8-MOP. In the latter situation, the 8-MOP would be more available for decontamination.

EXAMPLE 4

Artuc and co-workers examined the solubility of 8-MOP in human and bovine serum proteins. They showed that, when working with 8-MOP concentrations ranging from 100 to 1000 ng/ml in serum, 75% to 80% of the 8-MOP was bound to albumin. M. Artuc et al., Brit. J. Derm. 101:669 (1979).

In this example, the binding of 8-MOP to Calf Thymus DNA is compared using plasma and a protein free media in order to validate the efficiency of psoralen-nucleic interactions under the decontamination methods of the present invention. Although this measurement used eukaryotic nucleic acid rather than bacterial nucleic acid, it is a useful indicator of the degree of adduct formation for bacteria.

$^3$H-8-MOP was prepared to a concentration of 115 μg/ml in ethanol at a specific activity of $4.7 \times 10^6$ CPM/microgram (hereinafter "8-MOP stock"). Thereafter 130.5 or 22 μl of 8-MOP stock (2 each) for samples containing DNA ("+DNA") and 52.2 or 8.7 μl for samples not containing DNA ("−DNA") were dried down. To +DNA samples, 40 μl of DNA stock (7.7 mg/ml) was added as well as either 460 μl plasma (day old frozen) or 450 μl Tris-EDTA ("TE") buffer. To the latter was also added 10 μl 5M NaCl. For −DNA samples (i.e., the controls), 184 μl plasma and 16 μl water was added.

The samples were mildly vortexed for approximately one hour and the counts were checked to confirm that the 8-MOP is dissolved.

Each sample (100 μl) was irradiated on an HRI-100 (HRI Research Inc., Concord, Calif.) at 25° C. for 0, 2, 4, 8, and 16 minutes. Samples were kept at 4° C. overnight after irradiation. Thereafter, the samples were extracted. First, a phenol solution was prepared at pH 8 by equilibrating with 0.1 M Tris pH 8. Each sample was then extracted with 100 μl phenol. Each sample was centrifuged for 5 minutes to remove the aqueous phase to a new tube. A second extraction was performed with 100 μl 1:1 phenol:chloroform. A final extraction was performed with 100 μl chloroform.

The final aqueous phase was precipitated by adding 50 μl NaCl adjusted to give a final concentration of NaCl of 0.2 M and then adding 250 μl ethanol. The samples were again centrifuged (10 minutes). The supernatant was removed and the pellets were dried. The pellets were resuspended in 100 μl TE and reprecipitated. This was repeated for a total of 3 precipitations. The final pellets were brought up in 600 μl water and 100 μl was counted. Each sample was assayed for DNA by measuring absorbance (260 nm). 8-MOP levels were plotted as adducts per 1000 base pairs ("8-MOP:kBP").

Figure 6:
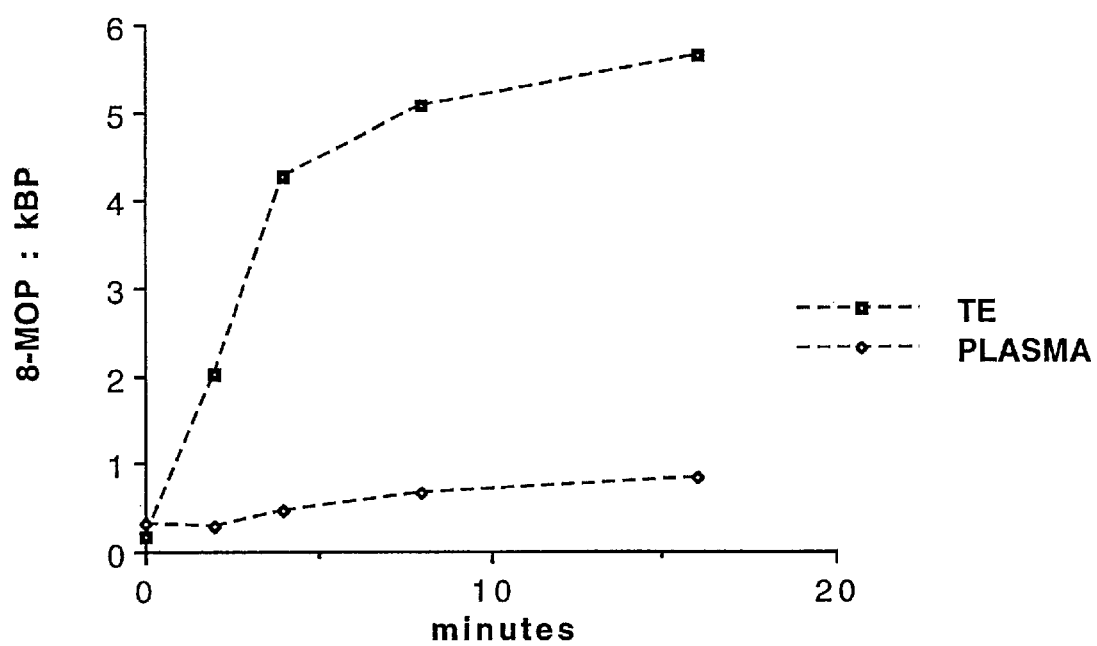
FIG. 6 is a graph showing the photoaddition of 8-methoxypsoralen to nucleic acid.

The results (FIG. 6) show that plasma does significantly change the addition kinetics of 8-MOP to DNA. Addition to nucleic acid is much better in the protein free media.

The frequency of 8-MOP-DNA adduct formation in protein free media predicts a high multiplicity of modification of the bacterial genome. Furthermore, this type of biochemical measurement has the potential to provide a means to monitor the efficiency of the photochemical inactivation method.

EXAMPLE 5

Photoactivation of psoralens and isopsoralens may result in a variety of photoproducts. "Photoproduct" is best understood by considering the possible reactions of photoreactive compound when exposed to activating wavelengths of electromagnetic radiation. While not limited to any precise mechanism, it is believed that the reaction of photoreactive compound in its ground state ("C") with activating wavelengths of electromagnetic radiation creates a short-lived excited species ("C*"):

C→C*

What happens next is largely a function of what potential reactants are available to the excited species. Since it is short-lived, a reaction of this species with nucleic acid ("NA") is believed to only be possible if nucleic acid is present at the time the excited species is generated. Thus, the reaction must, in operational terms, be in the presence of activating wavelengths of electromagnetic radiation, i.e., it is "photobinding"; it is not dark binding. The reaction can be depicted as follows:

C*+NA→NA:C

The product of this reaction is hereinafter referred to as "Photoaddition Product" and is to be distinguished from "Photoproduct."

With this reaction described, one can now consider the situation where nucleic acid is not available for binding at the time the compound is exposed to activating wavelengths of electromagnetic radiation. Since the excited species is short-lived and has no nucleic acid to react with, the excited species may simply return to its ground state:

$$C^* \rightarrow C$$

On the other hand, the excited species may react with itself (i.e., a ground state or excited species) to create a ground state complex ("C:C"). The product of these self-reactions where two compounds react is referred to as "photodimer" or simply "dimer." The self-reactions, however, are not limited to two compounds; a variety of multimers may be formed (trimers, etc.).

The excited species is not limited to reacting with itself. It may react with its environment, such as elements of the solvent ("E") (e.g., ions, gases, etc.) to produce other products:

$$C^* + E \rightarrow E:C$$

It is this type of reaction that is believed to cause cellular damage (e.g., reaction with oxygen to create singlet oxygen species). Furthermore, it may simply internally rearrange ("isomerize") to a ground state derivative ("["):

$$C^* \rightarrow [$$

Finally, the excited species may undergo other reactions than described here.

The present invention and the understanding of "photoproduct" does not depend on which one (if any) of these reactions actually occurs. "Photoproduct"—whatever its nature—is deemed to exist if, following the reaction of a compound and activating wavelengths of electromagnetic radiation, there is a resultant product formed that can interact with other components of the reaction environment.

With psoralens such as 4'-hydroxymethyl-4,5',8-trimethylpsoralen (HMT), there are a number of resultant products produced when the HMT is exposed to activating wavelengths of electromagnetic radiation. The major resultant products of HMT are two cyclobutyl photodimers. In one of the diners, the two pyrone rings are linked in a cis-syn configuration, while in the other dimer, the linkage occurs between the furan end of one molecule and the pyrone end of the other, again with cis-syn configuration. A third resultant product of HMT is a monomeric HMT photoisomer. In this isomer, the central ring oxygens assume a 1, 4 instead of the normal 1, 3 orientation. While the two photodimers would not be expected to have an intercalating activity due to geometrical considerations, the photoisomer remains planar, and accordingly, it is contemplated that it has a positive intercalative association with double stranded nucleic acid and, thus, could be a mutagen.

In this example, the photochemical breakdown of 8-MOP is compared with AMT. The samples were analyzed by reverse phase HPLC using a Rainen Dynamax 300A column. Gradient elution was performed with 0.1 M ammonium acetate / acetonitrile (0–70% acetonitrile over 42 minutes). AMT elutes as a single peak at approximately 24 minutes under these conditions. Detection was by absorption at either 260 or 330 nm. The latter wavelength was used for the plasma containing samples.

Standard solutions of each compound were prepared at various concentrations. These solutions were then diluted 1:10 into water, then 300 µl injected for analysis. All samples were monitored at 300 nm. Peaks were analyzed by measuring either peak height or peak area, then converted to a µh/ml value using the standard plot. Peak area was determined by photocopying the trace, cutting out the copy of the peak, then weighing the resultant trace. The two methods gave essentially the same result.

Figure 7:
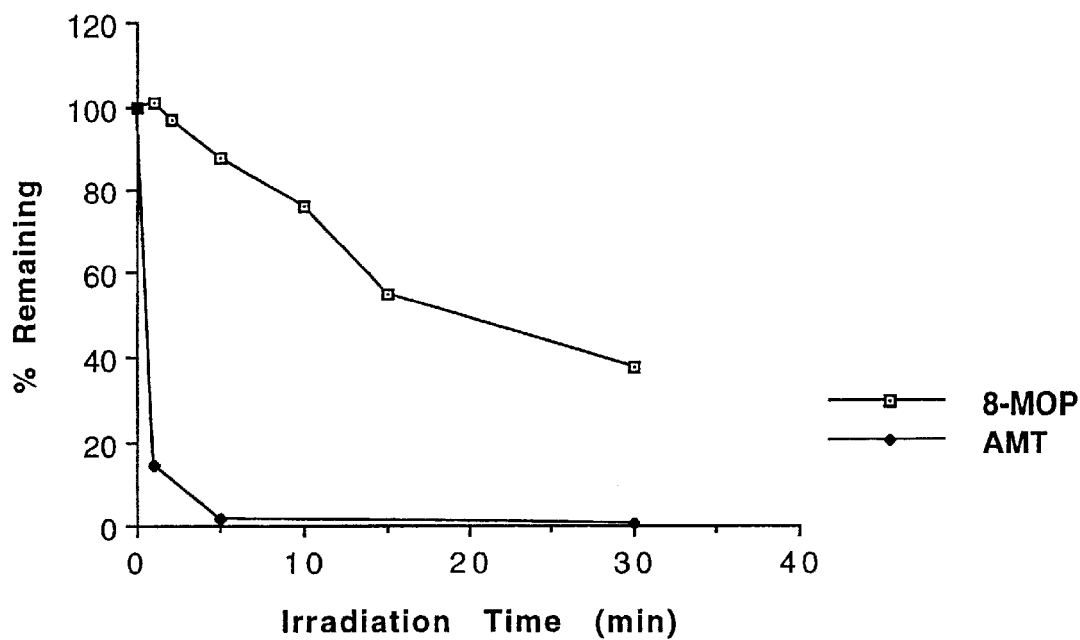
FIG. 7 is a graph showing the degradation of 8-methoxypsoralen (8-MOP) compared to that of 4'-aminomethyl-4,5',8-trimethylpsoralen (AMT), as measured by HPLC.

The results are shown in FIG. 7. Clearly, AMT degrades more quickly than 8-MOP. It would, therefore, be expected to generate more photoproducts—which eventually would end up in the transfusion recipient. By contrast, it is not expected that 8-MOP generates a significant amount of photoproducts. This is important when one considers that the weight of authority has concluded that unactivated 8-MOP is nonmutagenic.

EXAMPLE 6

Figure 9A:
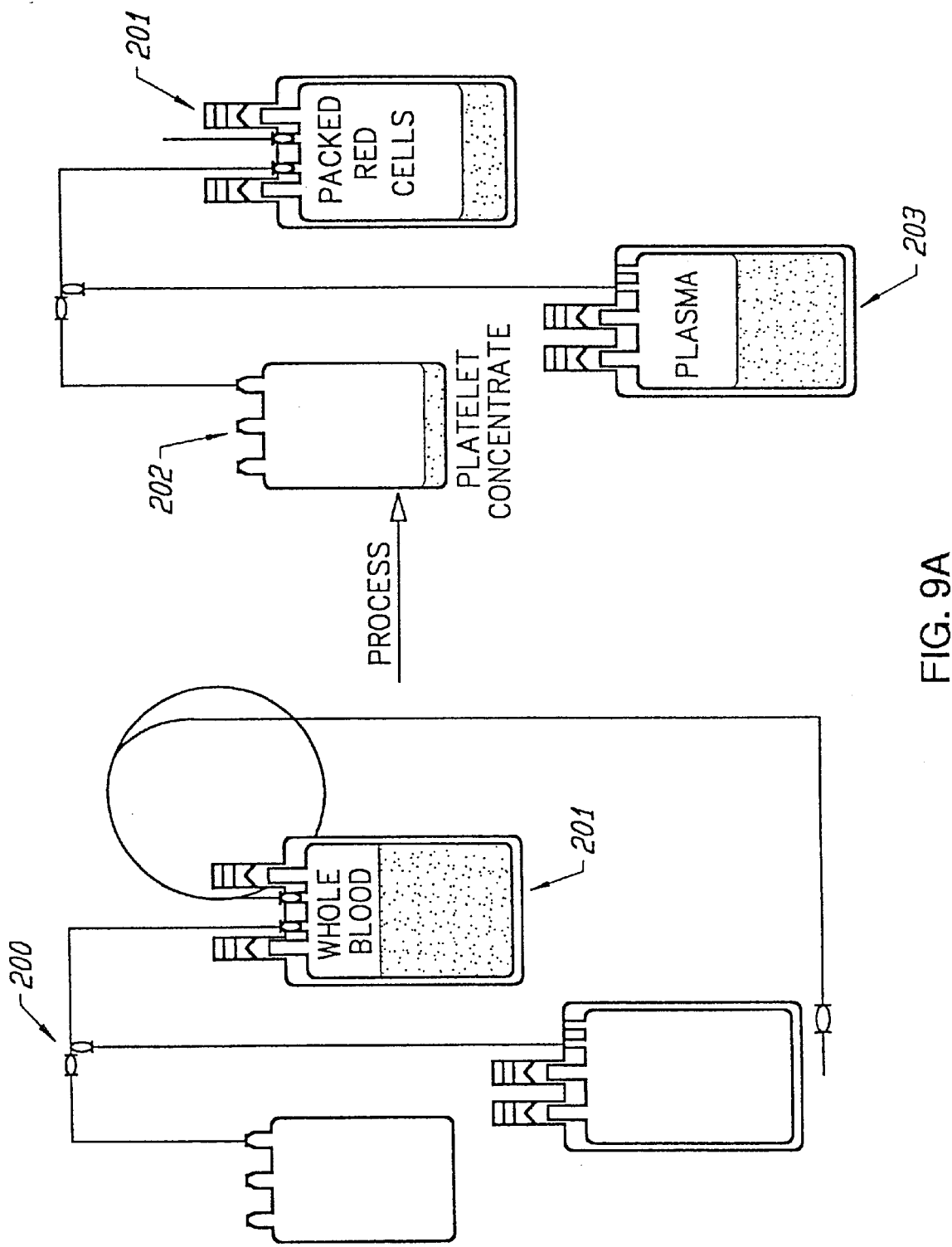
FIG. 9A schematically shows the standard blood product separation approach used presently in blood banks.

FIG. 9 shows an embodiment wherein platelets are diluted with synthetic media by the method of the present invention. FIG. 9A schematically shows the standard blood product separation approach used presently in blood banks. Three bags are integrated by flexible tubing to create a blood transfer set (200) (e.g., commercially available from Baxter, Deerfield, Ill.). After blood is drawn into the first bag (201), the entire set is processed by centrifugation (e.g., Sorvall™ swing bucket centrifuge, Dupont), resulting in packed red cells and platelet rich plasma in the first bag (201). The plasma is expressed off of the first bag (201) (e.g., using a Fenwall™ device for plasma expression), through the tubing and into the second bag (202). The first bag (201) is then detached and the two bag set is centrifuged to create platelet concentrate and platelet-poor plasma; the latter is expressed off of the second bag (202) into the third bag (203).

Figure 9B:
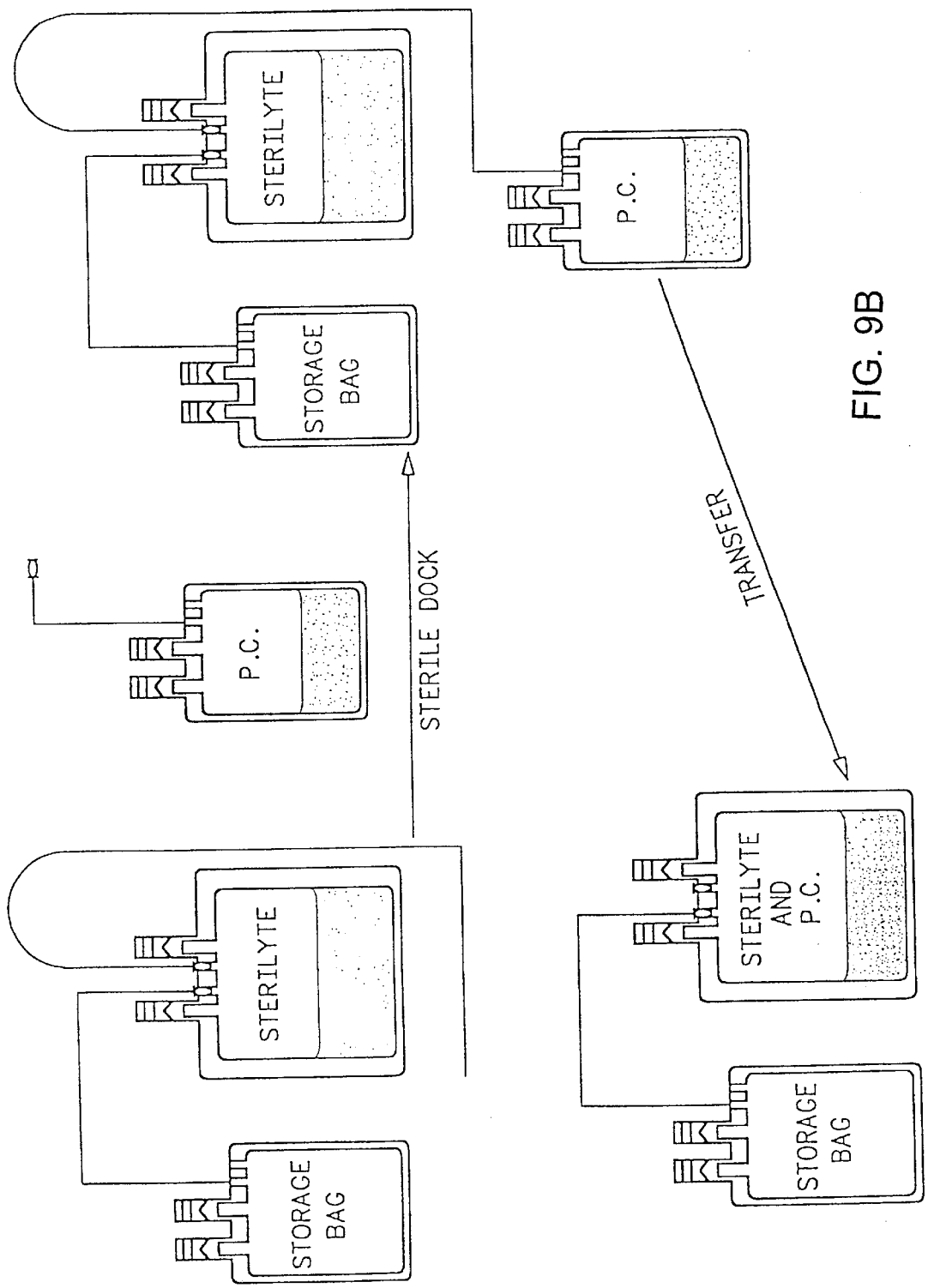
FIG. 9B schematically shows an embodiment of the present invention whereby synthetic media is introduced to platelet concentrate prepared as in FIG. 9A.

FIG. 9B schematically shows an embodiment of the present invention by which synthetic media is introduced to platelet concentrate prepared as in FIG. 9A. A two bag set (300) is sterile docked with the platelet concentrate bag (202) (indicated as "P.C."). Sterile docking is well-known to the art. See e.g., U.S. Pat. No. 4,412,835 to D. W. C. Spencer, hereby incorporated by reference. See also U.S. Pat. Nos. 4,157,723 and 4,265,280, hereby incorporated by reference. Sterile docking devices are commercially available (e.g., Terumo, Japan).

One of the bags (301) of the two bag set (300) contains a synthetic media formulation of the present invention (indicated as "STERILYTE"). In the second step shown in FIG. 9B, the platelet concentrate is mixed with the synthetic media by transferring the platelet concentrate to the synthetic media bag (301).

Figure 9C:
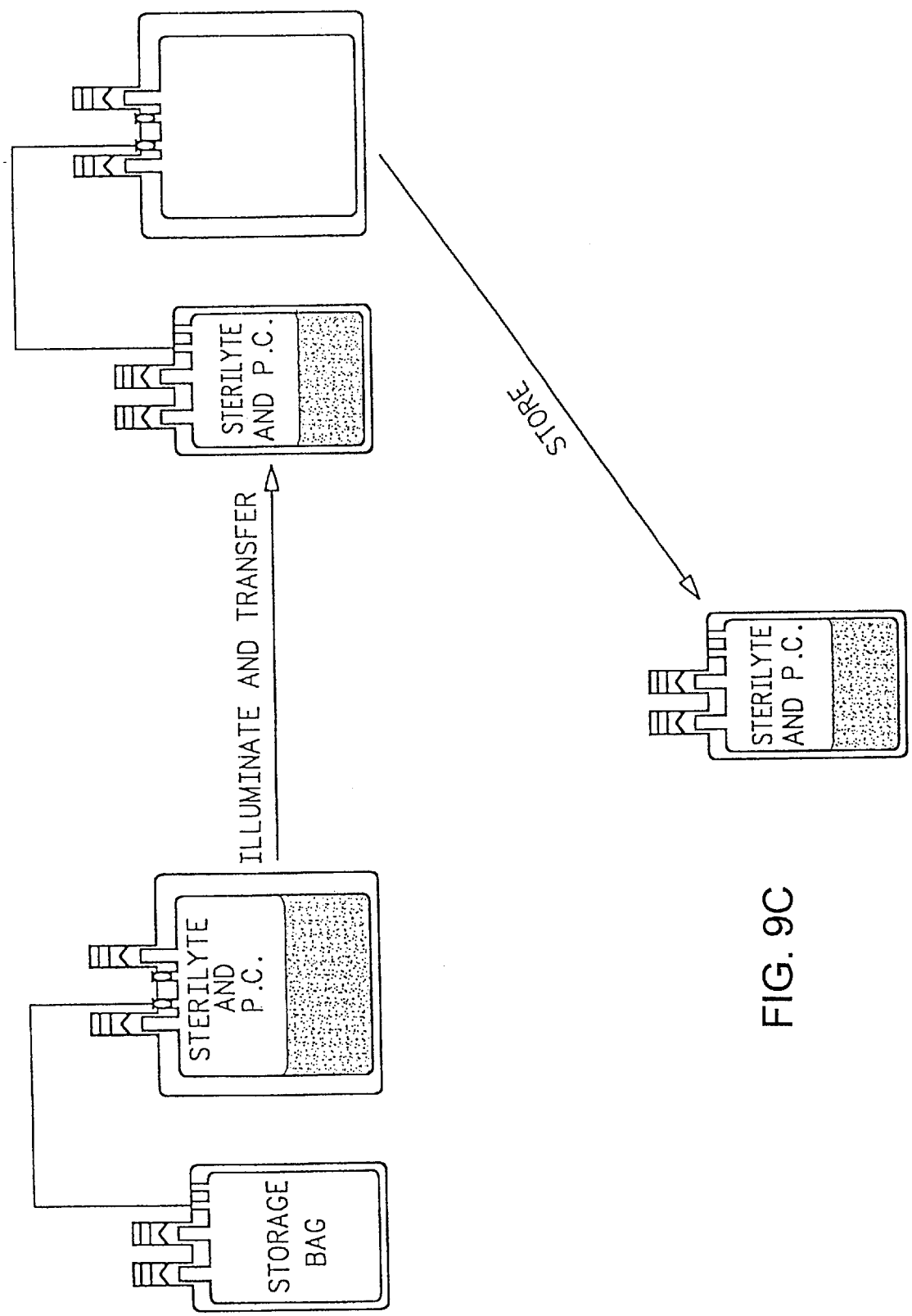
FIG. 9C schematically shows one embodiment of the decontamination approach of the present invention applied specifically to platelet concentrate diluted with synthetic media as in FIG. 9B.

FIG. 9C schematically shows one embodiment of the decontamination approach of the present invention applied specifically to platelet concentrate diluted with synthetic media as in FIG. 9B. In this embodiment, platelets have been transferred to a synthetic media bag (301) containing a nucleic acid binding compound. This bag (301), which has UV light transmission properties and other characteristics suited for the present invention, is then placed in a device (such as that described in Example 1, above) and illuminated.

Following phototreatment, the platelets are transferred from the synthetic media bag (301) into the storage bag (302) of the two bag set (300). The storage bag can be a commercially available storage bag (e.g., CLX bag from Cutter).

From the above, it should be evident that the present invention provides synthetic media formulations for use with blood preparations intended for storage and in vivo use. The formulations include synthetic media formulations to be employed in conjunction with the photodecontamination of platelets.

We claim:

1. A synthetic platelet storage media substantially free of glucose, comprising an aqueous solution of:
   45–120 mM sodium chloride;
   5–15 mM sodium citrate;
   20–40 mM sodium acetate;
   20–30 mM sodium phosphate;
   and a psoralen at a concentration greater than 0 and below its maximum solubility in water.

2. The synthetic platelet storage media of claim 1 wherein said media has a pH of approximately 7.2.

3. A synthetic platelet storage media substantially free of glucose, comprising an aqueous solution of:
   approximately 86 mM sodium chloride;
   approximately 10 mM sodium citrate;
   approximately 30 mM sodium acetate;
   approximately 26 mM sodium phosphate;
   and a psoralen at a concentration greater than 0 and below its maximum solubility in water.

4. The synthetic platelet storage media of claim 3 wherein said media has a pH of approximately pH 7.2 and an osmolarity of approximately 300 mOsm/Kg.

5. A synthetic platelet storage media, substantially free of glucose, comprising an aqueous solution of:
   approximately 86 mM sodium chloride;
   approximately 10 mM sodium citrate;
   approximately 30 mM sodium acetate; and
   approximately 26 mM sodium phosphate.

* * * * *